United States Patent
Olsen et al.

(10) Patent No.: US 6,228,050 B1
(45) Date of Patent: May 8, 2001

(54) OVERFILL PROTECTION SYSTEMS FOR IMPLANTABLE DRUG DELIVERY DEVICES

(75) Inventors: James M. Olsen; Reginald D. Robinson, both of Plymouth; Chris Christiansen, Oakdale; Paul Kratoska, Brooklyn Park, all of MN (US)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/303,006

(22) Filed: Apr. 30, 1999

(51) Int. Cl.$^7$ .................................................. A61M 11/00
(52) U.S. Cl. .................................... 604/93.01; 604/288.03
(58) Field of Search ........................ 604/93.01, 131–133, 604/141, 143, 174–175, 244, 247, 256, 890.1, 891.1, 30, 31, 33, 48, 151–153, 249, 288.01, 288.03; 251/318–322

(56) References Cited

U.S. PATENT DOCUMENTS

| | | | |
|---|---|---|---|
| 4,832,054 | * | 5/1989 | Bark . |
| 4,978,338 | * | 12/1990 | Melsky et al. ........................... 604/93 |
| 5,158,547 | | 10/1992 | Doan et al. . |
| 5,242,406 | * | 9/1993 | Gross et al. ........................... 604/132 |
| 5,665,070 | * | 9/1997 | McPhee ................................ 604/131 |

* cited by examiner

Primary Examiner—Richard K. Seidel
Assistant Examiner—LoAn H. Thanh

(74) Attorney, Agent, or Firm—Banner & Witcoff, Ltd.

(57) ABSTRACT

The displacement of refill valves in an implantable drug delivery device is reduced to permit the housings of a drug delivery device to remain compact in size while permitting reservoirs of increased depth to be used. In a preferred embodiment, a collapsible link is provided as a telescoping member incorporating a coil spring. As the valve is pulled into contact with its seat, a detectable pressure increase is sensed in the refill device. In accordance with the invention, as the drug supply contained in the reservoir depletes, the reservoir surface moves towards a collapsed position, compressing the coil spring and eventually contacting the valve stem, thereby lifting the valve from its seat. By virtue of telescoping link, the valve stem length and therefore the valve travel may be reduced as compared to prior art devices, thus eliminating the need for increased housing depth when deeper reservoirs are used. The collapsible link may be comprised of a second spring combined with a telescoping link. The second spring is situated on a side of the valve opposite the telescoping link, thereby providing a downward force on the valve and valve stem. As an other alternative, the invention provides a lever arm for actuating the refill valve. A pivot for the lever arm is situated near the refill valve and a distal end of the lever arm maintained in contact with the reservoir surface using a spring bias. An intermediate portion of the lever arm engages the valve stem. Thus, as the reservoir surface moves towards the collapsed position, the displacement of the valve is a fraction of the displacement of the distal end of the lever arm.

24 Claims, 7 Drawing Sheets

- PRIOR ART -

OVERFILL PROTECTION SYSTEMS FOR IMPLANTABLE DRUG DELIVERY DEVICES

BACKGROUND OF THE INVENTION

Field of the Invention

The present invention relates generally to implantable drug delivery devices. More particularly, the invention relates to overfill protection systems for preventing the overfilling and over pressurization of a reservoir of an implantable drug delivery device.

Description of Related Art

Implantable drug delivery systems are in widespread use to provide site-specific and/or sustained delivery of beneficial agents to address adverse patient conditions. Such delivery systems may include implantable infusion pumps, which typically include a pressurized drug reservoir and some form of fluid flow control. One example of an implantable infusion pump is the SYNCHROMED™ pump manufactured by Medtronic, Inc. of Minneapolis, Minn.

Typically, implantable drug delivery devices are periodically refilled in situ and percutaneously using a refill device, such as a hypodermic syringe inserted into a refill chamber of the device. A common problem related to refilling is the potential for overfilling or over pressurization of the device. Typically, the clinician who refills the device must rely on tactile pressure to sense that the drug reservoir has been filled to capacity. Any additional fluid injected into the device beyond capacity of the reservoir may cause severe damage to the drug administration device and may cause other adverse consequences.

Prior art overfill prevention devices, such as those described in U.S. Pat. No. 5,158,547, the entire writing of which is incorporated herein by reference, are exemplified by FIG. 1, which is a cross-section of a drug delivery device in the form of an implantable infusion pump 10. Generally, a valve 12 having a rigid valve stem 14 is fastened, usually by welding, to an inner surface 16 of the pump diaphragm or bellows 18. As new drug supply is injected through the septum 20 using a refill device (not shown), the reservoir chamber 22 fills with drug and the surface 16 moves towards a full position (downward in FIG. 1). As the reservoir chamber 22 reaches capacity, the valve 12 is pulled into sealing engagement with a valve seat 26, resulting in a detectable increase in pressure in the refill device and preventing overfilling and/or over pressurization of the drug delivery device 10. Notably, in prior art devices, as the reservoir collapses, the valve 12 and valve stem 14 must travel within the pump housing 30 a distance approximately equal to the distance traveled by the surface 16 of the reservoir 18.

Large reservoir sizes are desirable because they permit more quantity of a given therapeutic agent to be stored in the device and reduce the amount of refills necessary for a given period of time. On the other hand, it is desirable to reduce or maintain the size of the "footprint" of the overall drug delivery device so as to increase the ease of implantation and reduce associated trauma to the living body. As the size of the power and flow control features of drug delivery devices becomes reduced, due to advances in the related arts, there is potential for larger size reservoirs without associated increases in the size of the overall delivery device. However, prior art overfill protection systems are characterized by valve displacement that is equal to the displacement of the reservoir surface and therefore require that the pump housing depth be increased to accommodate the increased valve displacement that would occur with reservoirs of increased depth. Thus, prior art devices present an obstacle to further reduction in delivery device size and increase in reservoir size.

What is needed is an overfill protection system for implantable drug delivery devices which addresses the aforementioned problems. Specifically, what is needed is an overfill protection system for an implantable drug delivery device that does not require an increase in housing depth when the reservoir depth is increased.

SUMMARY OF THE INVENTION

The present invention solves the aforementioned problems by providing an overfill protection system for an implantable drug delivery device that incorporates a link for moving a refill valve in response to movement of the reservoir surface, wherein the link provides for reduced travel or displacement of the valve compared to prior art devices.

In a preferred embodiment, the collapsible link is provided as a telescoping member, which may be formed as a coil spring that is situated partially around the valve stem, which is separate from the reservoir surface but positioned to contact the reservoir surface as the reservoir collapses. The dimensions of the coil spring are such that positive contact between the reservoir surface occurs before the coil spring is fully compressed. In operation, when the drug delivery device is refilled, the reservoir expands and the reservoir surface moves towards a full position. Since the coil spring is affixed to the reservoir surface, it eventually extends beyond its natural length and exerts a force on the valve. As the valve is pulled into contact with its seat, a detectable pressure increase is sensed in the refill device. In accordance with the invention, as the drug supply contained in the reservoir depletes, the reservoir surface moves towards a collapsed position, compressing the coil spring and eventually contacting the valve stem, thereby lifting the valve from its seat. By virtue of telescoping link, the valve displacement is less than the reservoir surface displacement, thus eliminating the need for increased housing depth when larger reservoirs are used.

In another preferred embodiment, the collapsible link includes a second spring combined with a telescoping link. The second spring is situated on a side of the valve opposite the telescoping link, thereby providing a downward force on the valve and valve stem. This embodiment eliminates the need for fastening the first spring of the telescoping member to the reservoir surface and provides for reduced construction costs and increased dependability.

Still another aspect of the invention provides a lever arm for actuating the refill valve. A pivot for the lever arm is situated near the refill valve and a distal end of the lever arm maintained in contact with the reservoir surface using a spring bias. An intermediate portion of the lever arm engages the valve stem. Thus, as the reservoir surface moves towards the collapsed position, the displacement of the valve is a fraction of the displacement of the distal end of the lever arm.

The unique advantages provided by the invention reduce the displacement of refill valves in an implantable drug delivery device. Thus, housings of drug delivery device according to the invention need not be configured to accommodate valve displacement in an amount that is equal to the reservoir surface travel. Accordingly, reservoirs of increased depth may be utilized without a corresponding increase in the housing size.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE INVENTION

As explained in more detail below, the present invention overcomes the above-noted and other shortcomings of known systems by providing an implantable drug delivery device that incorporates a linkage system for moving a refill valve in response to movement of a surface of the reservoir, whereby the displacement of the valve is less than the displacement of the reservoir surface.

Figure 1:
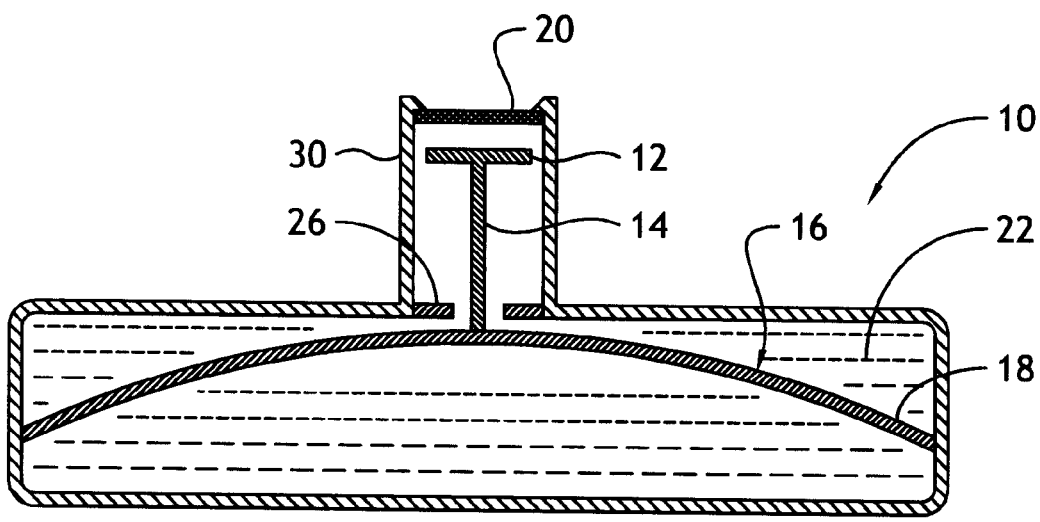
FIG. 1 is cross-section of an implantable infusion pump according to the prior art, as discussed above.
Figure 2A:
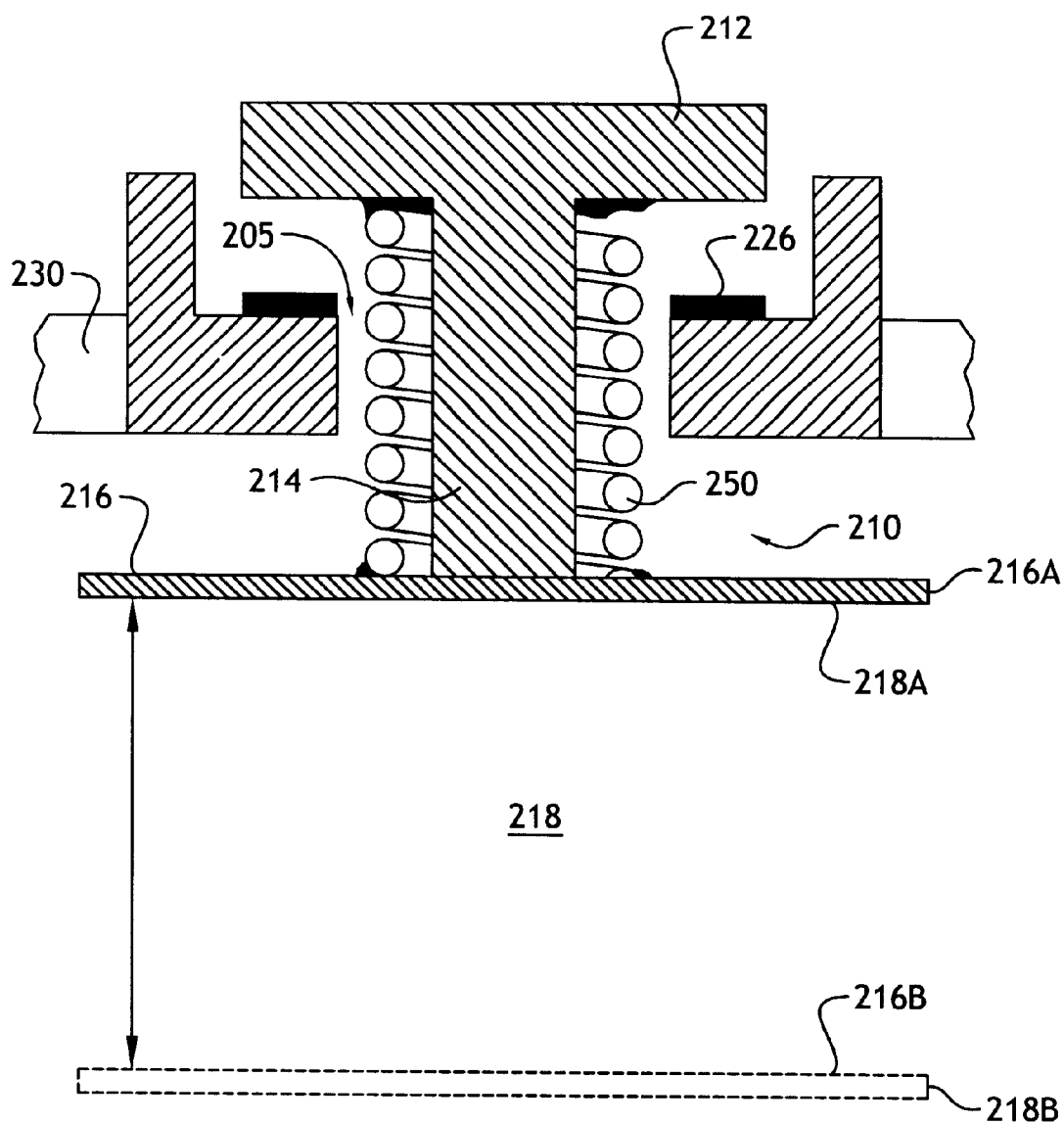
FIGS. 2A and 2B are cross-sections showing refill and full positions of an overfill protection system according to a preferred embodiment of the present invention.

Referring to FIG. 2A, according to a preferred embodiment of the invention, a linkage system, generally referenced 210, is comprised of a collapsible link that includes a telescoping member formed by the stem 214 of valve 212 and a coil spring 250. Valve 212 is movably mounted with respect to housing 230. One end of the coil spring 250 is affixed, for example by welding or adhesive, to a surface 216 of the reservoir 218. Reservoir surface 216 is shown in a refill position 216A in which the reservoir 218 is in a collapsed position and the drug supply (not shown) contained therein is depleted. It will be understood by those of ordinary skill that the reservoir surface 216 moves from refill position 216A to full position 216B as a new supply of drug or therapeutic agent is introduced through refill port 205.

As shown in FIG. 2A, reservoir surface 216 engages the bottom of the valve stem 214 and maintains the valve 212 in a refill position, displaced from the seal 226 to permit ingress of drug through refill port 205. As will be understood by those of ordinary skill, the dimensions of coil spring 250 and valve stem 214 are selected such that positive contact between the valve stem 214 and reservoir surface 216 occurs before the fully compressed state of the coil spring 250 occurs. However, the invention and the scope of the claims appended hereto are intended to cover devices in which valve stem 214 may be dimensioned, or even eliminated, and the displacement of the valve 212 is caused by full or partial compression of the coil spring 250.

Figure 2B:
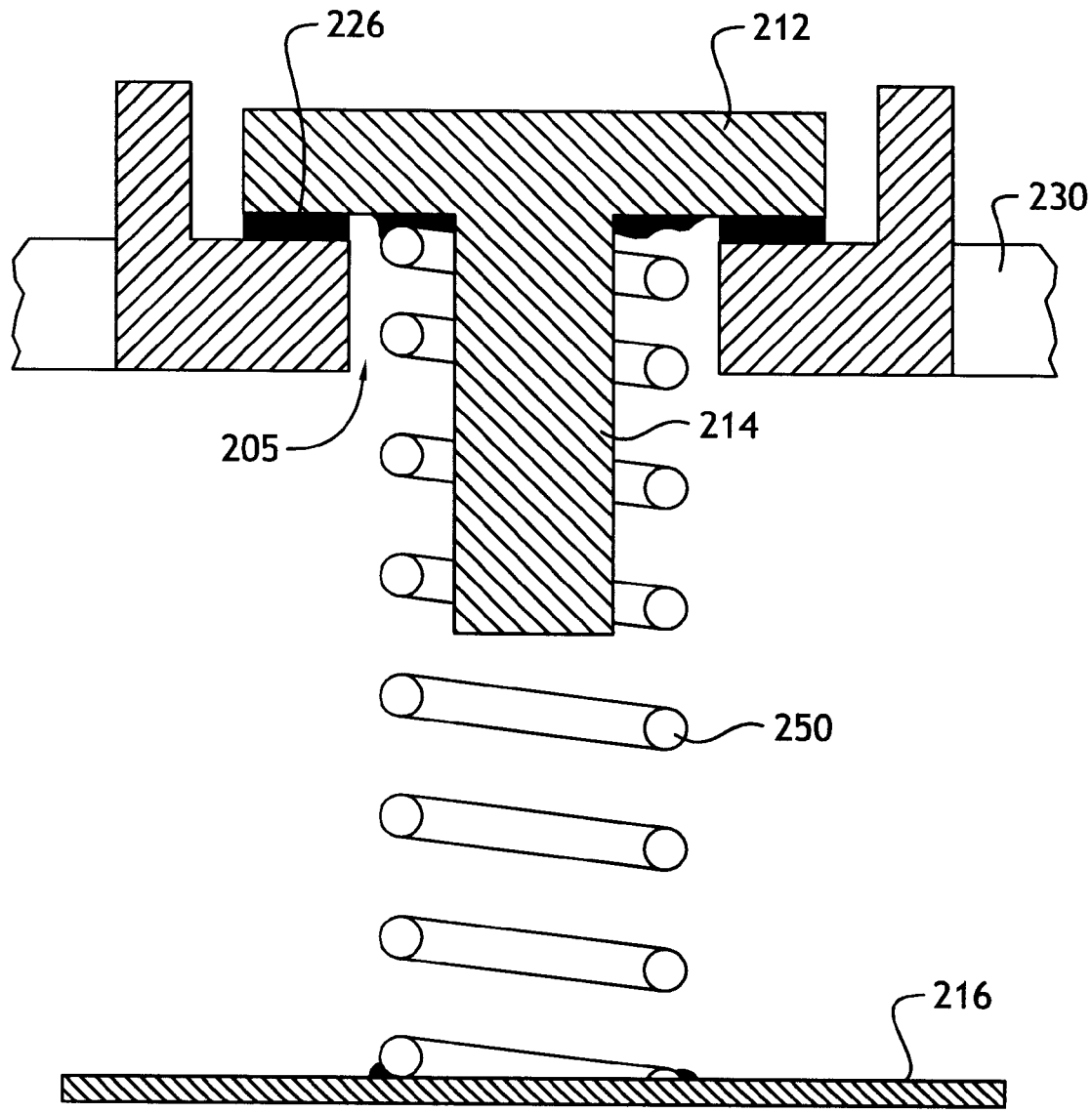

FIG. 2B illustrates the embodiment of FIG. 2A wherein reservoir surface 216 has moved to the full position. Coil spring 250 is extended beyond its natural length. As used herein, the term "natural length" refers to the length of a member when no external forces are applied to it. Coil spring 250 is therefore in tension so as to exert a force (downward in FIG. 2A) on the valve 212. As will be appreciated by those of ordinary skill, the upper end of coil spring 250 is affixed to the valve and/or valve stem 214 using known fastening techniques or devices, such as welding, adhesives or fasteners.

As shown in FIGS. 2A and 2B, in accordance with a primary feature of the invention, the displacement of the valve 212 is significantly less than the displacement of the reservoir surface 216 as the surface 216 travels from its full position to its collapsed position. Thus, the dimensions, i.e., the depth in a vertical direction of FIG. 2A, of delivery device housing 230 may be significantly reduced since valve displacement is reduced. Thus, the telescoping member is one means for moving valve 212 a second distance in response to movement of the reservoir surface, the second distance being less than the first distance.

Figure 3:
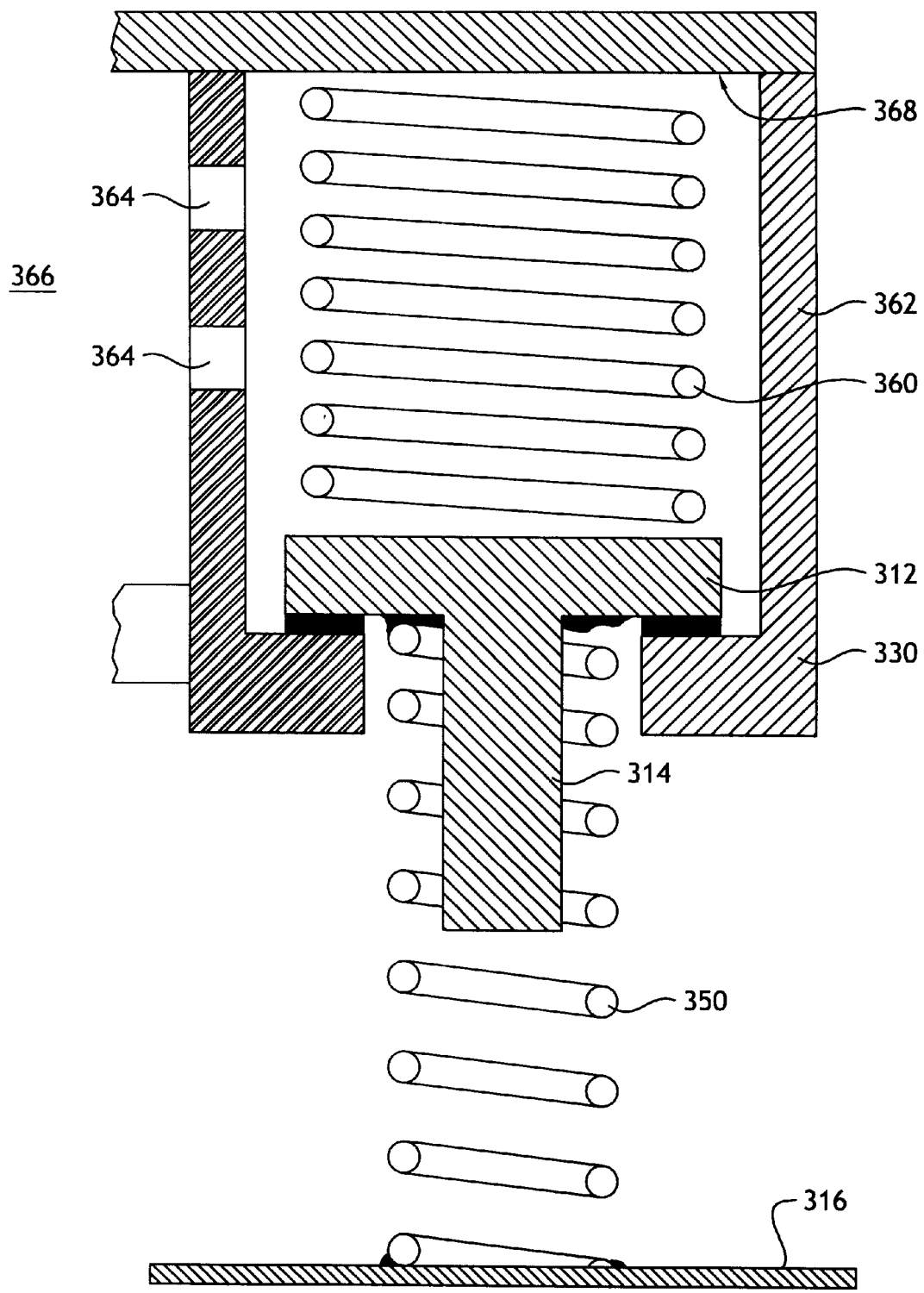
FIG. 3 is a cross section of an overfill protection system according to another preferred embodiment of the invention.

FIG. 3 illustrates another preferred embodiment of the invention, in which the welding or fastening of the coil spring 350 to the reservoir surface 316 is not necessary. Typically, the reservoir is constructed of rather thin metal material and welding may be problematic in certain circumstances. In this embodiment, a second coil spring 360 is provided in a spring chamber 362 formed in the delivery device housing 330. Fluid containing therapeutic agent is introduced into the spring chamber 362 via ports 364 which communicate with a refill chamber 366 having a septum (not shown) for receiving a refill agent (not shown). Spring chamber 362 includes a spring engagement surface 368 for engaging an upper end of second coil spring 360.

It will be recognized that the second spring 360 provides a sealing force (downward in FIG. 3) on a top surface of valve 312. Moreover, the characteristics of second spring 360 and first spring 350 are such that the stiffness of second spring 360 is less than the stiffness of the first spring 350. However, first spring 350 is always in compression, or at its natural length, regardless of the respective positions of valve 312 and reservoir surface 316 so that contact between the terminal ends of first spring 350 and valve 312 and reservoir surface 316 is maintained, thereby eliminating the need for fastening implements.

Figure 4:
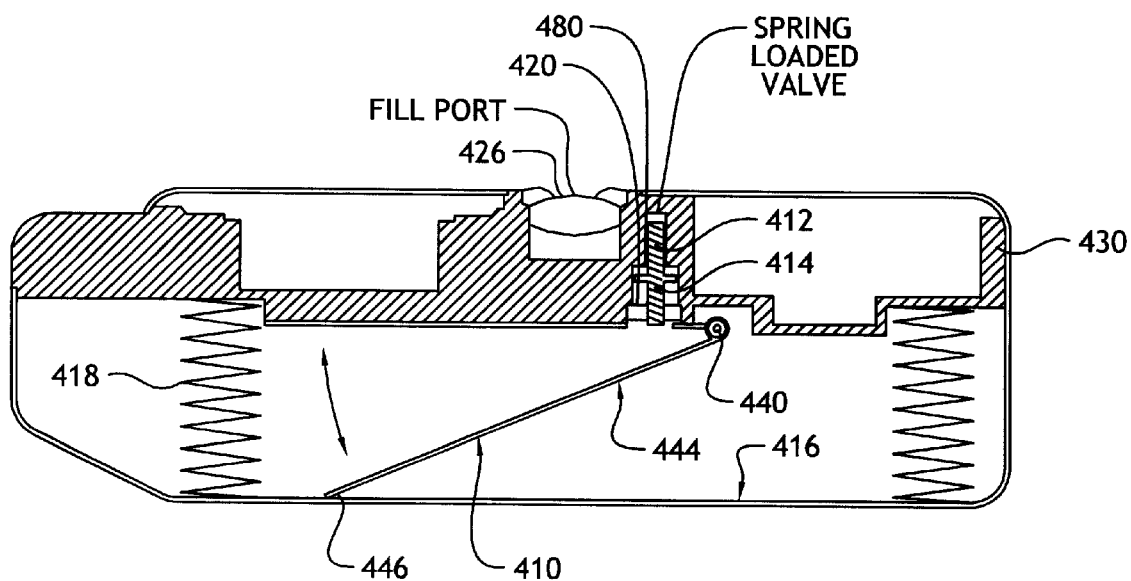
FIG. 4 is a cross section of an overfill protection system according to yet another embodiment of the invention.

FIG. 4 illustrates yet another preferred embodiment of the present invention. A lever arm 410 rests against the surface 416 of the reservoir, in this case a collapsible bellows 418. Lever 410 is pivotally secured to the delivery device housing 430 using a pivot pin 440. An intermediate portion 444 of lever arm 410 is between pivot pin 440 and the a distal end 446 of the lever arm 410 and is arranged to contact the stem 414 of valve 412, which is biased against its sealing surface 426 using a coil spring 480.

In operation, as the bellows 418 collapses, the distal end 446 of lever arm 410 moves towards a refill position, and intermediate portion 444 actuates valve 412 upward to remove it from the sealing surface 426 to permit refilling through the septum 420. As the bellows is refilled with new drug fluid and bellows reservoir 418 moves towards a full position, lever arm 410 moves downward and permits valve 412 to reseat against its sealing surface 426. It will be recognized, the embodiment illustrated in FIG. 4 eliminates the need for welding the lever 410 to the reservoir surface 416. Moreover, consistent with the advantages of the invention, the displacement of valve 412 is less than the displacement of the surface 416 of the reservoir as it moves from a filled position to a collapsed position. Thus, the housing of the delivery device may be formed as a compact structure, while permitting the use of larger bellows.

Figure 5A:
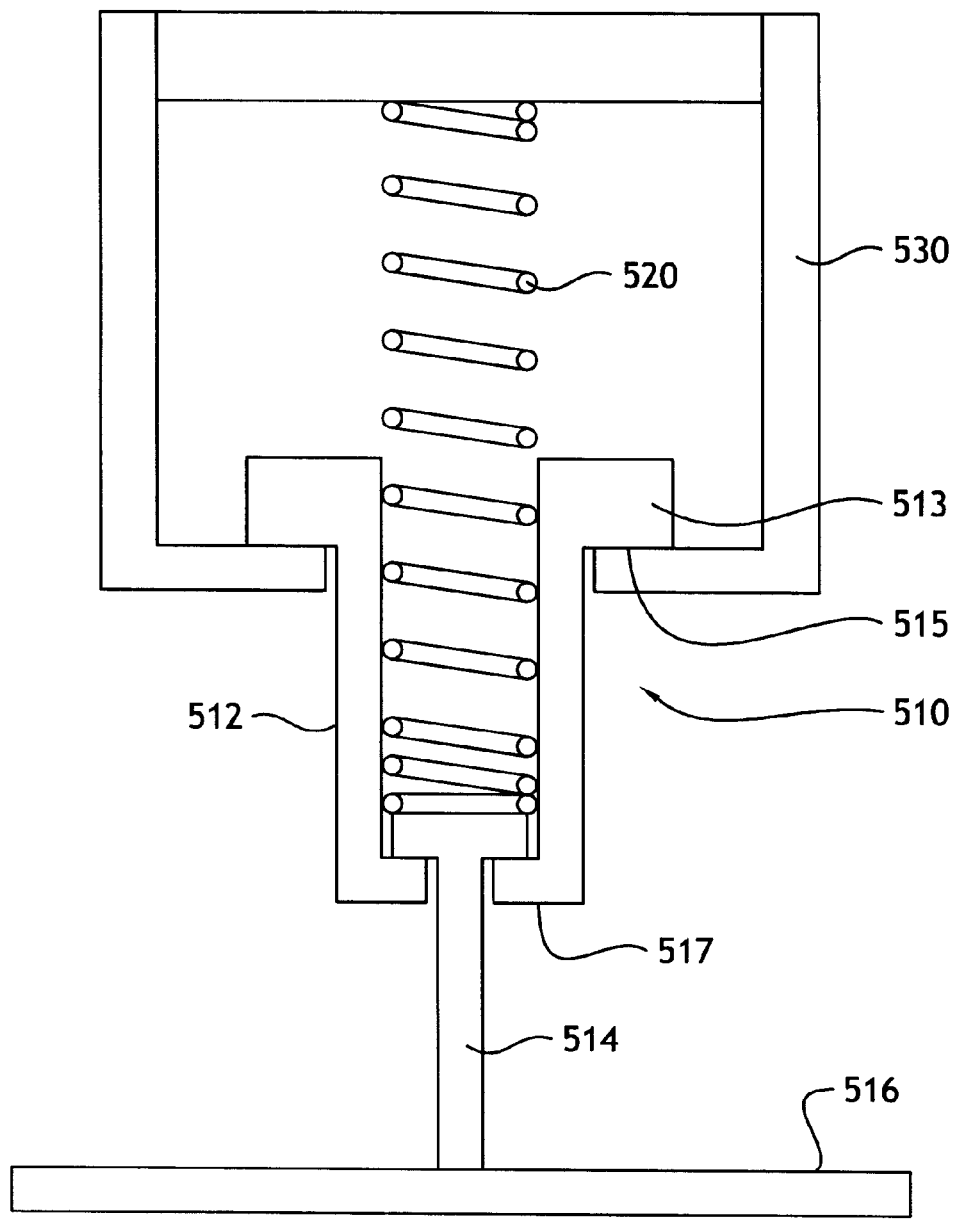
FIGS. 5A and 5B are cross-sections of an overfill protection system according to yet another embodiment of the invention.
Figure 5B:
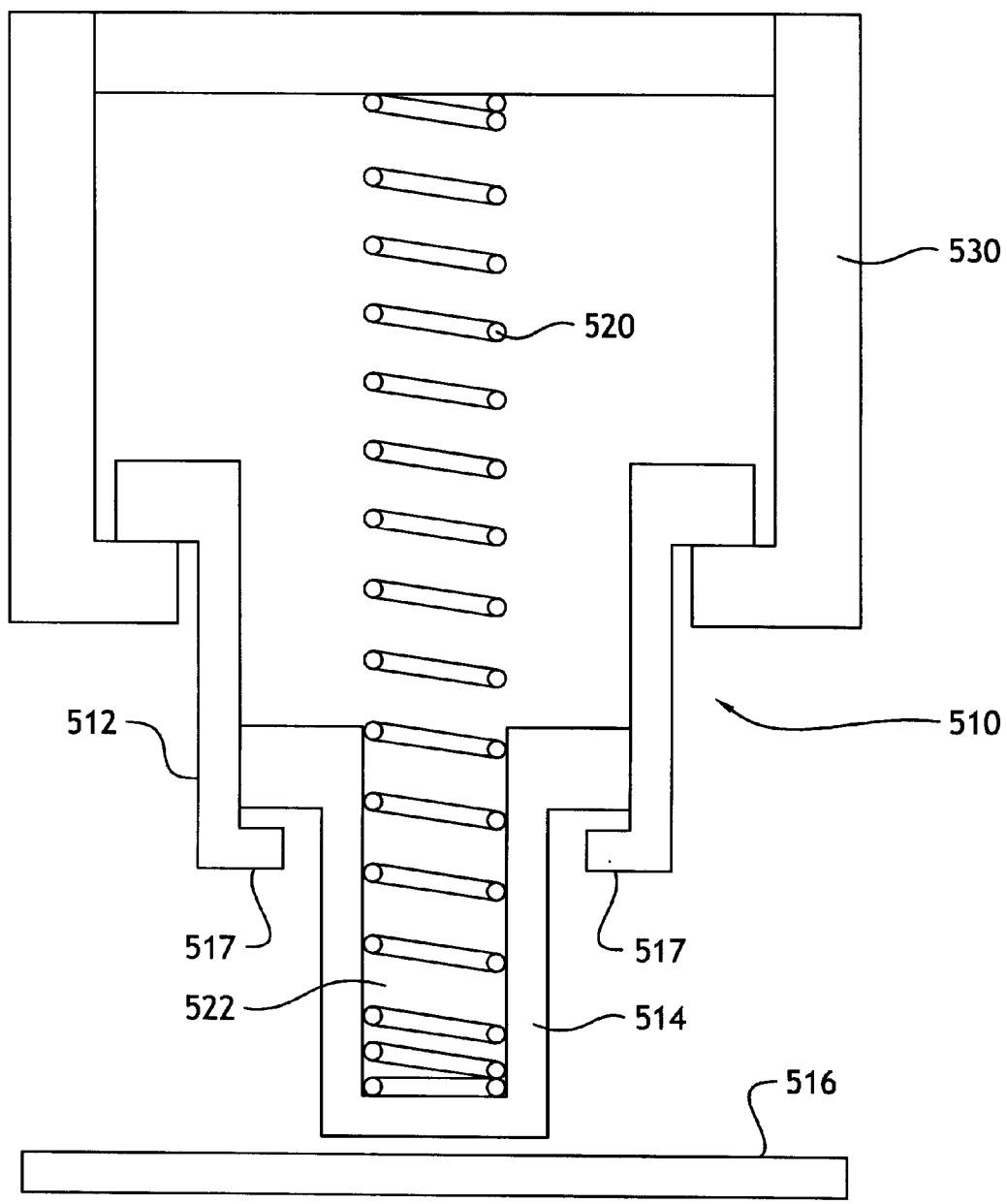

FIGS. 5A and 5B illustrate yet another embodiment of the invention. Collapsible link 510 is formed as a telescoping device which includes a first generally cylindrical telescoping member 512, movably mounted with respect to the housing 530, and a second, generally cylindrical telescoping member 514, movably mounted within the first telescoping member 512. The first telescoping member 512 is provided with an annular extension 513 which form a seal with an annular shoulder 515 of the housing 530. The second telescoping member 514 is provided with annular extension which sealingly engages a shoulder 517 formed in the first telescoping member 512. Thus, the telescoping members may each act as a valve element, which prevents ingress of drug when in their fully extended position (shown in FIGS. 5A and 5B, with exaggerated clearances between the sealing surfaces). On the other hand, when the bellows surface 516 moves from its expanded, full position, the telescoping members move with respect to one another so as to permit ingress of a refill supply of drug. In the embodiment shown in FIG. 5A, the spring 520 extends within the first telescoping member 512 and abuts a flat surface of the second telescoping member 514, which is configured as a solid element. In the embodiment in FIG. 5B, the second telescoping member 514 is provided with a recess 522 for receiving a portion of the spring 520.

Although the preferred embodiment of this invention has been described hereinabove in some detail, it should be appreciated that a variety of embodiments will be readily available to persons utilizing the invention for a specific end use. For example, the collapsible link of the present invention may be constructed using other spring forms, for example, gas springs or springs incorporating resilient plastics or polymers. The description of this invention is not intended to be limiting on this invention, but is merely illustrative of the preferred embodiment of this invention. Other products, apparatus and methods which incorporate modifications or changes to that which has been described herein are equally included within this application. Additional objects, features and advantages of the present invention will become apparent by referring to the above description of the invention in connection with the accompanying drawings.

What is claimed is:

1. An implantable drug delivery device comprising:
   a) a housing;
   b) a reservoir disposed within the housing for storing a supply of fluid and including a surface that moves a first distance as the reservoir collapses from a full position to a refill position;
   c) a refill port, formed in the housing, for receiving said fluid;
   d) a refill passage in the housing for conveying fluid from the refill port to the reservoir;
   e) a valve for selectively occluding the refill passage; and
   f) means for moving the valve a second distance in response to movement of the reservoir surface, the second distance being less than the first distance.

2. The device of claim 1, wherein the means for moving comprises a telescoping member.

3. The device of claim 2, wherein the telescoping member comprises a first spring.

4. The device of claim 3, wherein the first spring is adapted to exert a tension force on the valve when the reservoir surface is in the full position.

5. The device of claim 3, wherein the first spring is fastened to the reservoir surface.

6. The device of claim 3, further comprising a second spring adapted to provide a sealing force on the valve.

7. The device of claim 6, wherein the first spring is adapted to be maintained in compression during movement of the reservoir surface and valve.

8. The device of claim 1, wherein the means for moving comprises a lever.

9. The device of claim 8, wherein an end of the lever is pivotally mounted to the housing.

10. The device of claim 9, wherein a distal end of the lever, opposite the pivotally mounted end, engages the reservoir surface.

11. The device of claim 8, wherein the valve is biased towards a sealed position.

12. An implantable drug delivery device comprising:
    a) a housing;
    b) a reservoir disposed within the housing for storing a supply of fluid and including a surface that moves as the reservoir collapses from a full position to a refill position;
    c) a refill port, formed in the housing, for receiving said fluid;
    d) a refill passage in the housing for conveying fluid from the refill port to the reservoir;
    e) a valve for selectively occluding the refill passage; and
    f) a link operatively connecting the valve to the reservoir surface such that the displacement of the valve is less than the displacement of the reservoir surface.

13. The device of claim 12, wherein the link comprises a telescoping member.

14. The device of claim 13, wherein the telescoping member comprises a first spring.

15. The device of claim 14, wherein the first spring is adapted to exert a tension force on the valve when the reservoir surface is in the full position.

16. The device of claim 14, wherein the first spring is fastened to the reservoir surface.

17. The device of claim 14, further comprising a second spring adapted to provide a sealing force on the valve.

18. The device of claim 17, wherein the first spring is adapted to be maintained in compression during movement of the reservoir surface and valve.

19. The device of claim 12, wherein the means for moving comprises a lever.

20. The device of claim 19, wherein an end of the lever is pivotally mounted to the housing.

21. The device of claim 20, wherein a distal end of the lever, opposite the pivotally mounted end, engages the reservoir surface.

22. The device of claim 20, wherein the valve is biased towards a sealed position.

23. The implantable drug delivery device of claim 1, wherein the means for moving the valve is positioned between the valve and the reservoir surface.

24. The implantable drug delivery device of claim 12, wherein the link is positioned between the valve and the reservoir surface.

* * * * *